Figure 1:
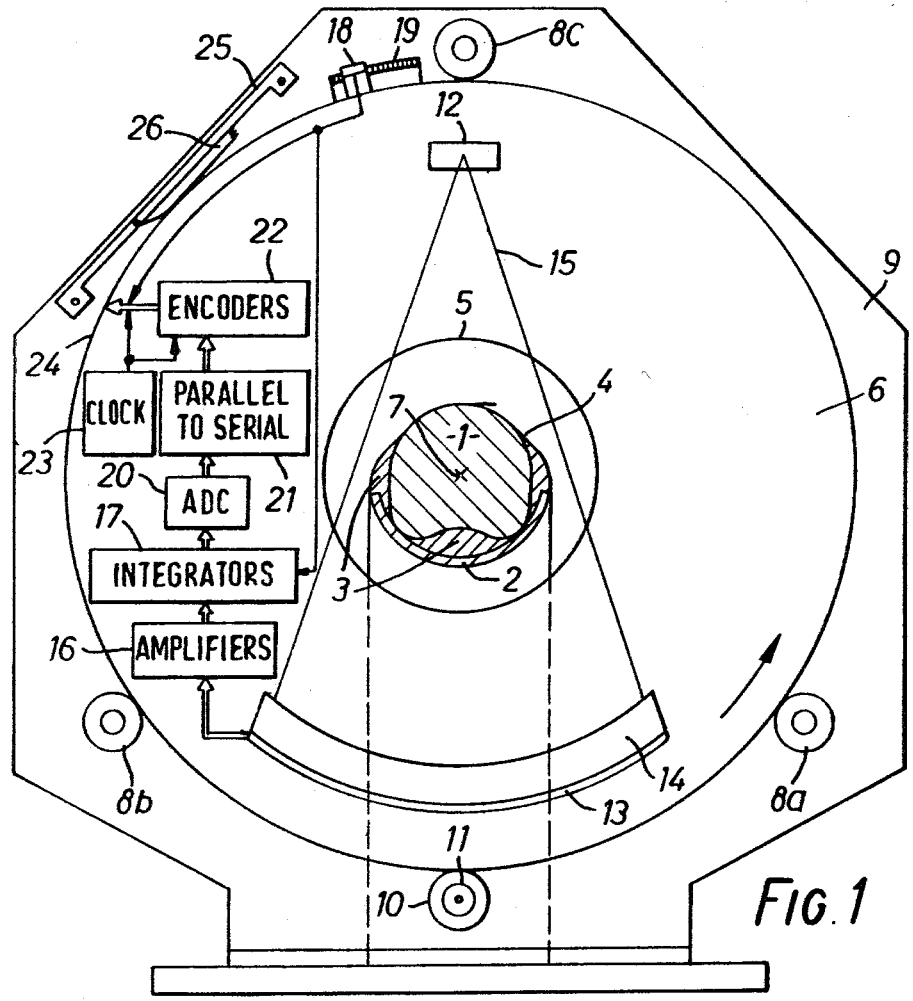

United States Patent [19]

Fairbairn

[11] 4,181,850
[45] Jan. 1, 1980

[54] DATA TRANSMISSION IN RADIOGRAPHIC APPARATUS

[75] Inventor: Ian A. Fairbairn, Maidenhead, England

[73] Assignee: EMI Limited, Hayes, England

[21] Appl. No.: 942,373

[22] Filed: Sep. 14, 1978

Related U.S. Application Data

[63] Continuation of Ser. No. 773,760, Mar. 2, 1977, abandoned.

[30] Foreign Application Priority Data

Mar. 3, 1976 [GB] United Kingdom ............... 8418/76

[51] Int. Cl.² .................. A61B 6/02; G01N 23/08
[52] U.S. Cl. ........................ 250/445 T; 250/360; 339/5 M; 340/207 P
[58] Field of Search .............. 339/5 M, 5 R, 5 P; 340/203, 207 R, 207 P; 250/360, 445 T; 178/67

[56] References Cited

U.S. PATENT DOCUMENTS

| | | | |
|---|---|---|---|
| 2,509,931 | 5/1950 | Krantz | 339/5 M |
| 3,970,853 | 7/1976 | Kuhl | 250/445 T |
| 3,983,399 | 9/1976 | Cox et al. | 250/445 T |
| 3,999,073 | 12/1976 | Hounsfield et al. | 250/445 T |
| 4,093,859 | 6/1978 | Davis et al. | 250/445 T |

*Primary Examiner*—Alfred E. Smith
*Assistant Examiner*—T. N. Grigsby
*Attorney, Agent, or Firm*—Cooper, Dunham, Clark, Griffin & Moran

[57] ABSTRACT

In radiographic apparatus in which a source of radiation and detectors receiving the radiation are orbited about a position for locating a patient, the examination can be carried out using a rotation through 360° or more. This arrangement uses slip rings for carrying data, including the output of the detectors and provides a slip ring arrangement suitable for high speed use. The slip rings can have capacitative coupling to avoid data loss if the brushes are allowed to bounce and for use therewith the data should be encoded in a D.C.-component-removing digital code.

12 Claims, 7 Drawing Figures

DATA TRANSMISSION IN RADIOGRAPHIC APPARATUS

This is a continuation, of application Ser. No. 773,760 filed Mar. 2, 1977 and now abandoned.

The present invention relates to the transmission of data in scanning radiographic apparatus from equipment for data acquisition mounted on moving parts thereof to processing equipment provided separately or mounted on fixed parts.

In U.S. Pat. No. 3,778,614 there is described apparatus for examining a body by means of penetrating radiation including a source of a beam of the radiation and a detector means arranged to measure the intensity of the radiation after passage through the body. Means are provided for moving the source and detector means through a predetermined angle to irradiate the body from a plurality of directions. Processing means for the data thus obtained are also disclosed.

For the movement described in that specification it is possible to provide relatively conventional data connections from the moving parts.

A further development of the apparatus, described in U.S. Pat. No. 3,937,963 and further described in United States application No. 544,799 allows a relatively faster motion of source and detector means about the body by irradiating the body along a plurality of beams of radiation disposed in a fan. In practice only a limited rotation (normally less then 360°) of the source and detector means is required thus allowing the continued use of conventional data transmission by means such as cables. However greater speed of examination can be obtained if the rotation extends through many revolutions thus allowing a high rotational velocity to be obtained before the examination commences. Thus data transmission for such apparatus should preferably allow continuous rotation of the part of the apparatus carrying the source and detector means.

It is an object of the present invention to provide a suitable data transmission arrangement.

According to the invention there is provided radiographic apparatus for examining a section of the body of a patient, the apparatus including: a scanning member; a source of penetrating radiation carried by the scanning member and arranged to project the radiation to traverse a region in which the patient's body may be disposed; detector means, sensitive to the radiation, carried by the scanning member and arranged to receive the radiation after it has traversed the region; means for rotating the scanning frame about an axis intersecting the region; a fixed structure supporting the scanning member during motion comprising at least said rotation; a plurality of slip rings fixed in relation to either said scanning member or said fixed structure and a plurality of brushes, at least one brush cooperating with each slip ring, fixed in relation to the other of said scanning member or said fixed structure, the combination of slip rings and brushes being adapted to transmit data signals, including data signals from said detectors, to electrical connections on said fixed member during said rotation.

Preferably the data signals are encoded to a DC-component-removing digital code prior to said transmission.

Figure 5:
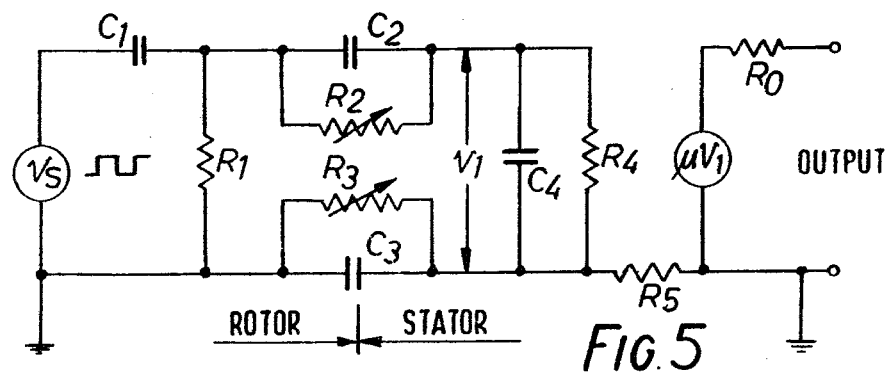
Figures 2A, 2B, 2C:
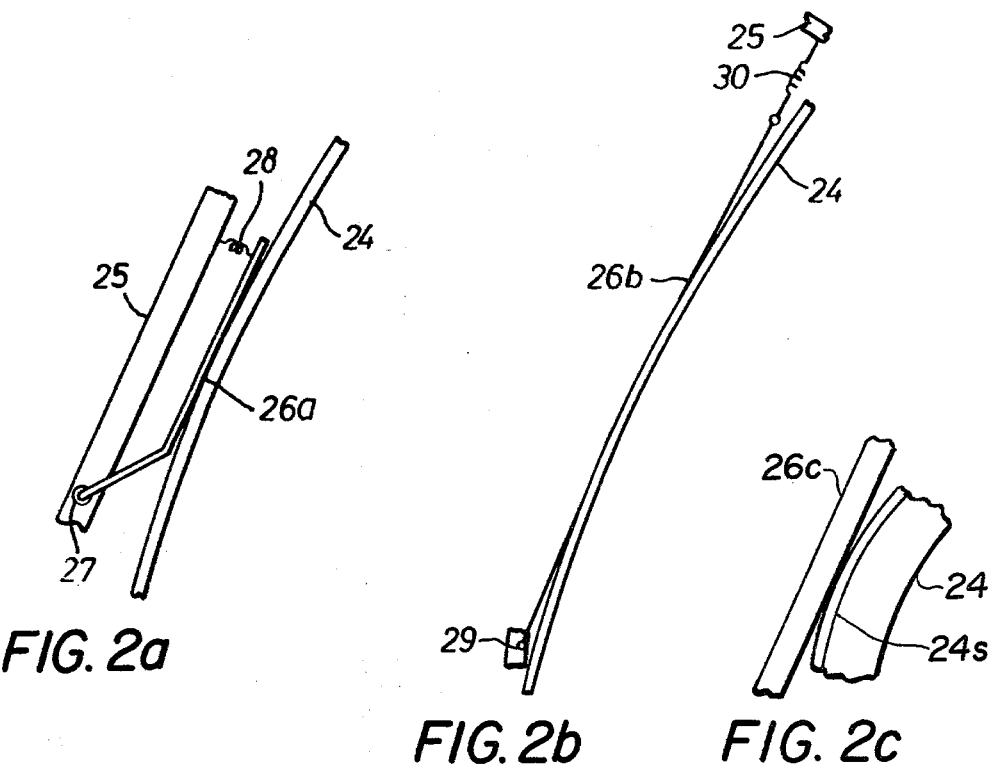
Figure 3:
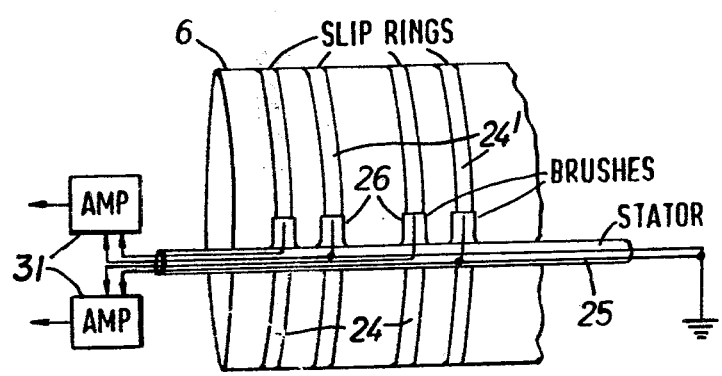
Figure 4:
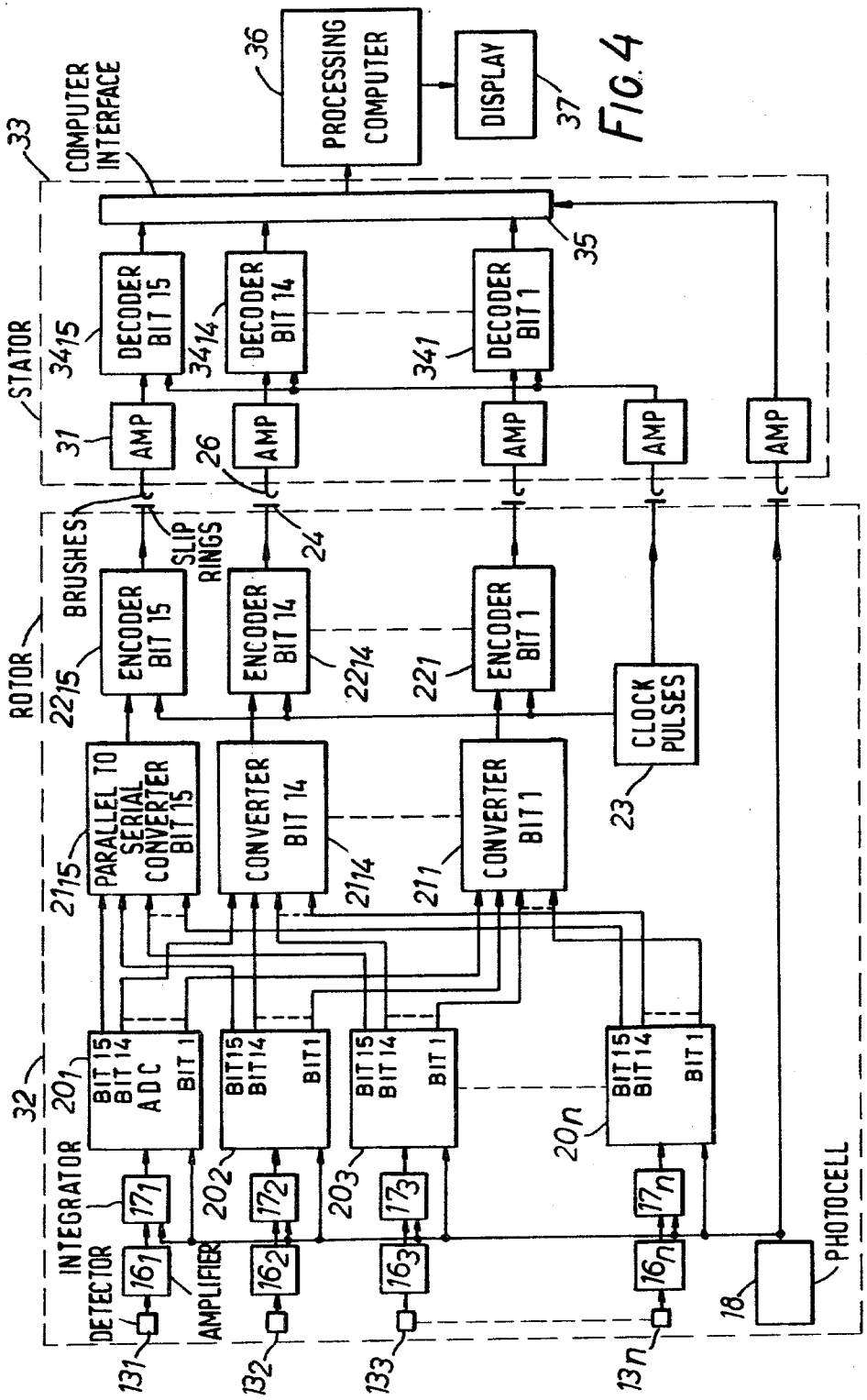

In order that the invention may be clearly understood and readily carried into effect an example thereof will now be described with reference to the accompanying drawings of which:

FIG. 1 shows an apparatus incorporating the invention,

FIGS. 2(a), 2(b) and 2(c) show suitable examples of brushes for the invention,

FIG. 3 illustrates in simplified form the arrangement of slip rings and brushes, FIG. 4 shows in block diagrammatic form the data transmission of the apparatus of FIG. 1 and FIG. 5 shows a typical slip ring/brush combination in the form of an equivalent circuit.

Referring to FIG. 1 there is shown apparatus in accordance with one example of the invention. A body 1, of a patient to be examined, is shown in transverse section supported on a suitably shaped bed 2, also shown in transverse section. A material 3, having an absorption to the radiation similar to that of body tissue, is positioned between the body 1 and bed 2, partly to support the patient and partly to exclude air from the gap therebetween, and is extended partly about the body to provide an approximately circular cross-section to the radiation. The material 3 may be water in one or more flexible bags or may be a viscous or particulate material. The body 1 is retained firmly in a desired position by means such as a retaining strap 4.

The bed 2 and the body 1 are inserted into an aperture 5 in a rotatable member 6 so that a chosen part of the body is centred in the aperture 5. Bed 2 may include supports on either or both sides of the member 6 but has been shown in the Figure to include supports only in the rear for the sake of clarity. The rotatable member 6 is arranged to rotate about an axis 7, which in this example is maintained longitudinal of the body and perpendicular to the paper. For that purpose it is supported by at least three gear wheels 8a,b,c, which engage gear teeth, not shown, cut in the periphery of member 6. The gear wheels 8 are journalled in a main frame 9 of the apparatus. In certain examples the member 6 may have an extent, perpendicular to the plane of the drawings, sufficient to require further support. In that case main frame 9, may, for example, have an aperture of sufficient extent to allow member 6 to extend therethrough to be supported at the opposite side by further wheels such as 8. A further gear wheel 10, also engaging the said gear teeth, is driven by an electric motor 11, also mounted on the main frame 9, and serves to provide the required rotary motion.

The rotatable member 6 also carries a source 12 of a fan of X-rays 15, a bank of detectors 13 and a bank of associated collimators 14. The source 12 may take many forms suitable to particular types of apparatus employing a continuous rotation. In this example a fixed source of X-rays is provided, the apparatus being essentially of the form described in U.S. Pat. No. 3,937,963. However source 12 may be of the type in which the source point, of the X-rays, is scanned across a fixed target/anode as is used, for example, in the apparatus described in United States application No. 630,779 or No. 733,941. The detectors, which in a typical embodiment number 200, can be of any suitable type, for example scintillation crystals with associated photomultipliers, photodiodes or proportional counters. In this example the source 12 and detectors 13 are substantially equidistant from axis 7, although this may be varied if desired provided the geometry of the arrangement is accurately known.

In operation source 12 irradiates the body 1 with the fan 15 of X-rays. In this example the X-rays originate from a substantially fixed point relative to the rotatable member 6. However in alternative arrangements electronic or mechanical scanning of the source point may be included. The X-rays are partially absorbed by the body and the intensity after such absorption is measured by detectors 13. Each detector receives radiation transmitted through the body along a respective beam defined by the dimensions of the associated arc of collimators 14. The output of each detector is provided to a respective independent one of amplifiers 16 where it is amplified for input to a respective integrator 17. The integrator integrates the signal for a period representing a predetermined degree of rotational motion to provide an analogue signal representing the total intensity of radiation incident on the respective detector in that time. This radiation has been transmitted through the body along a path effectively examined by that detector, taking into account the rotational motion. To provide information representing the rotation a position detector is provided. In this example the detector takes the form of a photocell and light source unit 18 mounted on member 6. This cooperates with a circular graticule 19 mounted on main frame 9 and concentric with member 6. The graticule, which extends through 360° although only a small part is illustrated for clarity, comprises a transparent substrate with opaque markings thereon. These interrupt a light path between the light source and photocell and provide thereby pulses indicative of the rotary motion. Other means of providing such pulses may, of course, be devised. The pulses are supplied to integrators 17 for controlling the setting and resetting thereof.

The analogue signals from integrators 17 are provided to respective ones of analogue to digital converters (ADC) 20 which provide them as digital signals of, in this example, 15 bits. In this example converters 20 also receive the pulses from unit 18, which are used to initiate conversion of each input from the respective integrator.

Thus far the apparatus is essentially the same as that described in U.S. Pat. No. 3,937,963. However in accordance with the invention it is proposed to transmit the absorption data from member 6 to stationary parts of the apparatus, for further processing, via slip rings, and for this purpose the data is transmitted in digital form. Thus amplifier 16, integrators 17 and ADC 20 are mounted on member 6. It will be understood that they may be so mounted in any convenient place, for example adjacent their respective detectors. For convenience therefore they have only been indicated in FIG. 1 in diagrammatic block form to one side of member 6.

For transmission the signals are also processed by parallel to serial converters 21 and encoders 22 which will be considered further hereinafter. Thence, together with the pulses from photocell unit 18 and pulses from a clock generator 23 they are applied to slip rings 24 formed on the periphery of member 6, which for the purposes of the slip rings may be termed the 'rotor'.

A sufficient number of slip rings are provided for the data to be transmitted. In this example there are two for each bit of the digital signals, plus slip rings for clock, position pulses and any further data desired to be transmitted.

Mounted on main frame 9 is a 'stator' 25 on which are fixed resiliently brushes 26, one for each slip ring 24.

Two possible arrangements of brushes are shown in FIG. 2. FIG. 2a shows a brush 26a which is a single piece of flexible metal, for example spring bronze leaf, hingedly mounted on the stator at 27 and pressed against the slip ring 24 by a spring 28.

In the alternative arrangement of FIG. 2b the brush 26b is a thin ribbon fixed to the stator at 29 and held under tension by a spring 30 such as to hold it against the slip ring 24. Other more complex forms of brush may be devised for the desired purpose.

FIG. 3 illustrates in simplified form the general arrangement. The rotor 6 carries slip rings 24 and 24', of which only four are shown. The stator 25 carries corresponding brushes 26, in this example of a different form. As mentioned above the slip ring and brushes are grouped in pairs, each 24 and 24' forming a data channel, and each such pair feeds a respective amplifier 31 where the signals are amplified prior to further processing. It should be understood that in FIG. 3, for the purposes of illustration, rotor 6 and slip rings 24 are not to the same scale as brushes 26 and stator 25. Clearly the brushes could be fixed to the rotor and the slip rings to the stator, if desired, and more than one brush could be used with each slip ring.

In general slip rings have not been considered to be suitable for data transmission from a device rotating at high speed, such as in the apparatus of FIG. 1, because variations of the contact resistance and even loss of contact may create spurious signals. The situation is improved if the contact is made by capacitive coupling between slip ring and brush rather than by direct metal-to-metal contact. If desired the brushes or slip rings may be provided with insulating surfaces such as shown at 24s in the detail drawing of FIG. 2c to prevent direct contact although that is not the case in the preferred example. Using capacitive coupling data transmission using one of many suitable codes can be satisfactory. However, during prolonged loss of contact such as may be caused by bouncing of the brush, DC levels on either side of the contact may drift apart. For this reason the data should be coded by a code suitable for AC coupled links. Although many such codes are known in the data transmission art, in this example the data is coded to phase-modulated dipulse transmission. This is a well known code in which a '1' is represented by a 1 followed by a 0 and a '0' by a 0 followed by a 1, so that each bit is represented by a pair of pulses having a zero crossing therebetween. Encoders and decoders for this code are readily available to those skilled in the art. The overall data handling circuits for the apparatus are shown in FIG. 4 in which those circuits mounted on the rotor are shown within the broken line 32 and those on the stator, including main frame 9, are shown within the broken line 33.

As shown hereinbefore each detector $13_1, 13_2 \ldots 13_n$ feeds a respective amplifier $16_1 \ldots 16_n$ and integrator $17_1 \ldots 17_n$, the integrators being set and reset by pulses from photocell unit 18. The integrators supply the analogue signals to ADC units $20_1, 20_2 \ldots 20_n$ at which they are converted to digital form as 15 bit signals in this example. Thus far the data signals on each channel have been independent with signals appearing in each simultaneously. At this point each bit of the data signals is applied to a respective unit 21 such that $21_1$ receives bits '1' from each ADC simultaneously and so on for the other units until, $21_{14}$ receives bits '14' simultaneously and $21_{15}$ bits '15' simultaneously. Units 21 are parallel-to-serial converters from which the data signals are further transmitted in serial form. Thus from this point a channel k from unit $21_k$ transmits the bits k for all detectors in sequence (1 to n) for an integration interval, and repeats the sequence for the next integration interval. Following this in each channel a respective DC component removing coder $22_{15} \ldots 22_1$ converts the data into the chosen code, in this example dipulse, for output at slip rings 24.

As mentioned hereinbefore, in this example the coupling is AC through two slip rings for each channel, one being at a reference potentially normally as earth return. Thus each slip-ring/brush combination shown in FIG. 4 actually represents a pair thereof.

Of course a common earth return can be used if required. However in this example an earth return ring ($24^1$ in FIG. 3) is provided between each pair of signal channels providing in effect guard rings to reduce cross-talk between channels. Electrically induced interference can be reduced by screening the slip rings by, say, an outer metal drum on the stator. Further slip rings are also provided for other data such as clock pulses and position indicator pulses.

From brushes 26 on stator 25 the data signals are applied via amplifiers 31 to respective decoders $34_{15} \ldots 34_1$ which restore the original form of the digital signals. Decoders 34 are, for this purpose, provided with clock pulses, from clock 23, which were also provided to encoders 22. The proper relationships between the pulses are thus maintained during coding and decoding. All digital data from decoders 34 is provided to a computer interface 35 from which it is transmitted to a processing computer 36 for processing to form the desired representation of absorption for display at 37. This processing may be by any suitable method such as that described in the said U.S. Pat. No. 3,778,614 or the convolution method described in U.S. Pat. No. 3,924,129. In addition the position identification pulses from unit 18 are also provided to the computer via interface 35 to aid in the proper organisation of the incoming data.

Turning once more to the slip rings and associated brushes it may be helpful to consider the operation of these in terms of a simple equivalent circuit, such as that of FIG. 5. In that Figure the voltage source $V_S$, capacitance $C_1$ and resistance $R_1$ represent the circuits prior to the slip rings. $C_2$, $R_2$ and $C_2$, $R_3$ represent slip ring to brush contacts, $R_2$ and $R_3$ being variable between 0 and infinity at opposite extremes of bounce. The other circuit components represent the respective differential amplifier 31 which is situated as close as possible to the respective brush.

For typical flat brushes, say 2 cm long by ½ cm wide about 20 pF capacity is obtained when separated from the slip ring by a bounce of about one thousandth of an inch. If the brushes are curved to fit the slip ring this capacity is much higher. The AC coupling mentioned hereinbefore involves a series capacitance $C_1$ one or two orders of magnitude greater than the brush/ring capacity, for example 10000 pF. Also typically $R_1$ is 50Ω. This gives a time constant long enough to cope with the longest data dipole pair expected.

The input resistance $R_4$ of the differential amplifier is greater than 10 kΩ and the capacitance $C_4$ less than, in this example 5 pF, which is a quarter of the brush capacity at the expected worse bounce.

A false pulse will be generated by bad contact resistance only if the resulting input to the amplifier drops to close to the voltage at the other input to the amplifier. The slip ring/brush capacitance can be thought of as the first element of a potential divider; the amplifier input capacitance, plus stray capacitances, comprise the second element. Good contact going to bad contact means that the first element goes from zero impedance to an impedance not greater than one quarter of the second element. The transmittance of the signal thus varies from unity to 66%. Thus in this example spurious signals should not be generated even if both brushes bounce together.

In the circuit of FIG. 5 the value of connection $R_5$ is not critical in view of the connection existing between rotor earth and stator earth via bearings and other paths.

Considering the other circuit elements:
$R_4 \gg$ Other impedances
$(1/2\pi f C_1 \ll R_1$
$C_2 \gg$ Other capacitances $$V_1 = V_S \cdot Z_4/(Z_2 + Z_3 + Z_4)$$

Therefore at bounce, when $R_2 = R_3 = \infty$ $$V_1' = V_S \frac{C_2 C_3}{C_2 C_3 + C_2 C_4 + C_3 C_4}, C_2 = C_3 = C$$

At good contact $R_2 = R_3 = 0$
therefore $V_1'' = V_S$
so the ratio $$V_1'/V_1'' = \frac{1}{1 + \frac{2C_4}{C}}$$

It will be appreciated that the invention is not limited to the apparatus described but can be used with any apparatus requiring the transmission of data from a component having a rotational component of motion. Other examples of suitable apparatus include those also providing a lateral component of motion.

In analysing the effects of the slip rings, on other circuits, they may be considered as transmission lines. From such analysis it will be seen that it is desirable to provide suitable termination resistors at some point on each loop between a slip ring 24 and the corresponding earth return ring 24' (FIG. 3). This termination resistance should determine the transmission line characteristics, rather than the brush impedance, so that those characteristics do not vary with the variable distances between the brushes and the slip ring input connections.

In an alternative embodiment the guard slip rings 24' are not provided with brushes and do not therefore function as slip rings but merely as the earth returns of the transmission lines formed in conjunction with corresponding slip rings 24. In that case guard rings 24' may be relatively thinner than the slip rings 24. One or more earth return slip rings (not shown) should also be provided as common earths for the data channels and all of the earth guard rings should be connected to them. Preferably two common earth slip rings are provided, one at each extreme of the series of data channel slip rings. Furthermore these common earth slip rings should each be provided with a plurality of brushes to reduce the effects of brush bounce, which would be more significant in the common earth return.

What I claim is:
1. Radiographic apparatus for examining a section of the body of a patient, the apparatus including: a scanning member; a source of penetrating radiation carried by the scanning member and arranged to project the radiation to traverse a region in which the patient's body may be disposed; detector means, sensitive to the radiation, carried by the scanning member and arranged to receive the radiation after it has traversed the region; means for rotating the scanning frame about an axis intersecting the region; a fixed structure supporting the scanning member during motion comprising at least said rotation; a plurality of slip rings fixed in relation to either said scanning member or said fixed structure and a plurality of brushes, at least one brush co-operating with each slip ring, fixed in relation to the other of said scanning member or said fixed structure to form a plurality of channels, a channel comprising at least two slip rings each co-operating with at least one brush, adapted to transmit signals, including data signals from said detectors, to electrical connections on said fixed member during said rotation, and encoder means adapted to encode the data signals according to a code suitable for AC as well as DC transmission.

2. An apparatus according to claim 1 wherein one slip ring in each channel is at a reference potential the overall arrangement being such that alternate slip rings are at the reference potential to provide shielding between adjacent channels.

3. Radiographic apparatus for examining a section of the body of a patient, the apparatus including: a scanning member; a source of penetrating radiation carried by the scanning member and arranged to project the radiation to traverse a region in which the patient's body may be disposed; detector means, sensitive to the radiation, carried by the scanning member and arranged to receive the radiation after it has traversed the region; means for rotating the scanning frame about an axis intersecting the region; a fixed structure supporting the scanning member during motion comprising at least the said rotation; a plurality of slip rings fixed in relation to either said scanning member or said fixed structure and a plurality of brushes, at least one brush co-operating with each slip ring, fixed in relation to the other of said scanning member or said fixed structure, the slip rings and brushes being arranged to have primarily capacitive coupling therebetween to transmit signals, including data signals from said detectors, to electrical connections on said fixed member during said rotation.

4. An apparatus according to claim 3 wherein the contact surfaces of at least the slip-rings or the brushes are coated with an insulating material to prevent a resistive coupling therebetween.

5. An apparatus according to claim 3 including means for converting the data, prior to transmission, into a code which does not include a D.C. component.

6. An apparatus according to claim 5 in which the said code is the phase modulated dipulse code.

7. Radiographic apparatus for examining a section of the body of a patient, the apparatus including: a scanning member; a source of penetrating radiation carried by the scanning member and arranged to project the radiation to traverse a region in which the patient's body may be disposed; detector means, sensitive to the radiation, carried by the scanning member and arranged to receive the radiation after it has traversed the region; means for rotating the scanning member about an axis intersecting the region; a fixed structure supporting the scanning member during motion comprising at least the said rotation; a plurality of slip rings fixed in relation to either said scanning member or said fixed structure and a plurality of brushes fixed in relation to the other of said scanning member or said fixed structure to form a plurality of channels adapted to transmit signals, including data signals from said detectors to electrical connections on said fixed member, wherein at least one of said brushes co-operates with a slip ring at a reference potential to form a return path and each of said channels comprises in combination one slip ring co-operating with at least one brush to form a signal path.

8. Apparatus according to claim 7 in which there is disposed between every two of the slip rings forming signal paths, a guard ring at the reference potential.

9. Radiographic apparatus for examining a section of the body of a patient, the apparatus including: a scanning member; a source of penetrating radiation carried by the scanning member and arranged to project the radiation to traverse a region in which the patient's body may be disposed; detector means, sensitive to the radiation, carried by the scanning member to receive the radiation after it has traversed the region and to provide output signals indicative of the intensity of the radiation received; means for rotating the scanning frame about an axis intersecting the region; a fixed structure supporting the scanning member during motion comprising at least the said rotation; a plurality of slip rings fixed in relation to either said scanning member or said fixed structure and a plurality of brushes, at least one brush co-operating with each slip ring, fixed in relation to the other of said scanning member or said fixed structure; encoding means adapted to encode data signals, including the detector output signal, or signals derived therefrom, for transmission via said slip rings and brushes, the encoding being according to a code suitable for transmission via a capacitative coupling which arises at least if one of said brushes temporarily loses contact with the respective slip ring.

10. An apparatus according to claim 9 wherein the encoding means is adapted to encode according to a code which does not include a D.C. component.

11. An apparatus according to claim 10 wherein the said code is the phase modulated dipulse code.

12. Radiographic apparatus for examining a section of the body of a patient, the apparatus including: a scanning member arranged to project the radiation to traverse a region in which the patient's body may be disposed; detector means, sensitive to the radiation, carried by the scanning member and arranged to receive the radiation after it has traversed the region to provide output signals indicative of attenuation of the radiation in the region; means for rotating the scanning member about an axis intersecting the region; a fixed structure supporting the scanning member during motion comprising at least the said rotation; encoding means for encoding data signals, including at least the said output signals or signals derived therefrom, into a code which does not include a D.C. component; a plurality of slip rings fixed in relation to either said scanning member or said fixed structure and a plurality of brushes fixed in relation to the other of said scanning member or said fixed structure, to form a plurality of channels adapted to transmit said encoded data signals.

* * * * *

UNITED STATES PATENT AND TRADEMARK OFFICE
CERTIFICATE OF CORRECTION

PATENT NO. : 4,181,850
DATED : January 1, 1980
INVENTOR(S) : IAN A. FAIRBAIRN

It is certified that error appears in the above-identified patent and that said Letters Patent are hereby corrected as shown below:

Column 6, line 15, delete "$C_2>>$" and insert -- $C_1>>$ --.

Signed and Sealed this

First Day of July 1980

[SEAL]

Attest:

SIDNEY A. DIAMOND

Attesting Officer — Commissioner of Patents and Trademarks